United States Patent
Xiao et al.

(10) Patent No.: US 8,822,680 B2
(45) Date of Patent: Sep. 2, 2014

(54) PARACYCLOPHANE-BASED LIGANDS, THEIR PREPARATION AND USE IN CATALYSIS

(75) Inventors: Jianliang Xiao, Liverpool (GB); Jiwu Ruan, Liverpool (GB)

(73) Assignee: Johnson Matthey PLC, London (GB)

( * ) Notice: Subject to any disclaimer, the term of this patent is extended or adjusted under 35 U.S.C. 154(b) by 1016 days.

(21) Appl. No.: 12/675,918

(22) PCT Filed: Aug. 21, 2008

(86) PCT No.: PCT/GB2008/050730
§ 371 (c)(1),
(2), (4) Date: Oct. 22, 2010

(87) PCT Pub. No.: WO2009/027729
PCT Pub. Date: Mar. 5, 2009

(65) Prior Publication Data
US 2011/0028718 A1    Feb. 3, 2011

(30) Foreign Application Priority Data
Aug. 29, 2007  (GB) .................................. 0716714.1

(51) Int. Cl.
| | | |
|---|---|---|
| *C07D 295/14* | (2006.01) | |
| *C07C 41/30* | (2006.01) | |
| *C07F 9/50* | (2006.01) | |
| *C07C 25/22* | (2006.01) | |
| *B01J 31/24* | (2006.01) | |
| *C07D 295/033* | (2006.01) | |
| *C07C 209/10* | (2006.01) | |
| *C07C 45/68* | (2006.01) | |
| *C07D 295/155* | (2006.01) | |
| *C07D 295/096* | (2006.01) | |

(52) U.S. Cl.
CPC ............. *B01J 31/2404* (2013.01); *C07C 41/30* (2013.01); *B01J 2231/4227* (2013.01); *C07F 9/5022* (2013.01); *C07C 2103/92* (2013.01); *C07C 25/22* (2013.01); *B01J 2531/828* (2013.01); *B01J 2231/4211* (2013.01); *C07D 295/033* (2013.01); *B01J 2531/827* (2013.01); *C07C 209/10* (2013.01); *C07C 45/68* (2013.01); *B01J 2231/4283* (2013.01); *B01J 2531/0263* (2013.01); *B01J 2531/821* (2013.01); *C07D 295/155* (2013.01); *B01J 2531/824* (2013.01); *B01J 2531/822* (2013.01); *C07D 295/096* (2013.01)
USPC ......................................................... 544/163

(58) Field of Classification Search
CPC ........................................................ C07F 15/00
USPC ......................................................... 544/163
See application file for complete search history.

(56) References Cited

FOREIGN PATENT DOCUMENTS

| WO | WO-97/47632 A1 | 12/1997 |
|---|---|---|
| WO | WO-01/74829 A1 | 10/2001 |
| WO | WO-02/057278 A1 | 7/2002 |
| WO | WO-2004/111065 A1 | 12/2004 |

OTHER PUBLICATIONS

Focken et al., Tetrahedron: Asymmetry 15 (2004) 1693-1706.*
Rozenberg et al., Tetrahedron Letters (2003), 44(19), 3801-3804.*
Forrester et al., J Chem Soc, Perkin 1(1975), (18), 1753-1757.*
Amthor et al., J Phys Chem A (2006), 110(3), 1177-1189.*
Focken, et al., Tetrahedron: Asymmetry 15 (2004) 1693-1706.*
Zanotti-Gerosa et al., "Phosphonites Based on the Paracyclophane Backbone: New Ligands for Highly Selective Rhodium-Catalyzed Asymmetric Hydrogenation," *Organic Letters*, 2001, vol. 3, No. 23, pp. 3687-3690.
Whelligan et al., "Synthesis of Pseudo-*germinal*-, Pseudo-*ortho*-, *ortho*-Phosphinyl-oxazolinyl-[2.2]paracyclophanes for Use as Ligands in Asymmetric Catalysis," *J. Org. Chem.*, 2006, 71, pp. 4606-4618.

(Continued)

*Primary Examiner* — Porfirio Nazario Gonzalez
*Assistant Examiner* — Kofi Adzamli
(74) *Attorney, Agent, or Firm* — RatnerPrestia

(57) ABSTRACT

A substituted paracyclophane is described of formula (I) wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl and Z is a substituted or unsubstituted alkyl group, aryl group or heteroaryl group. Preferably $X^1$ and $X^2$ are —($C_2H_4$)— and Z is a substituted aryl group. The substituted paracyclophane provides transition metal catalysts that are useful in C—C and C—N bond formation and asymmetric hydrogenation reactions.

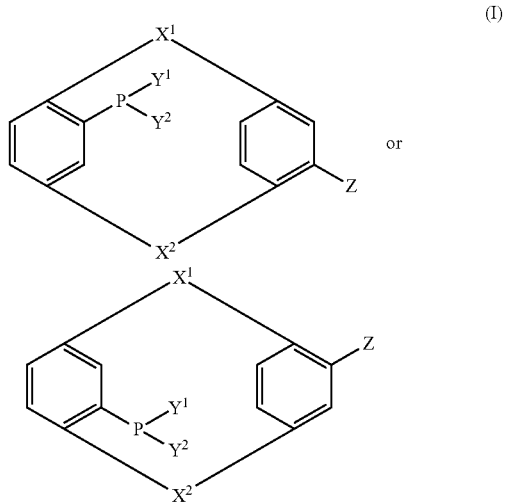

12 Claims, No Drawings

(56) References Cited

OTHER PUBLICATIONS

Rozenberg et al., "A novel class of bidentate ligands with a conformationally flexible biphenyl unit built into a planar chiral [2.2]paracyclophane backbone," *Tetrahedron Letters*, 2004, 44, pp. 3801-3840.

Gibson et al., "[2.2]Paracyclophane derivatives in asymmetric catalysis," *Org. Biomol. Chem.*, 2003, 1, pp. 1256-1269.

Forrester et al., "Nitroxide Radicals. Part XVII. Transannular Interactions in [2.2]Paracyclophanyl Nitroxides," *J. Chem. Soc., Perkin Trans.*, 1975, 1, pp. 1753-1757.

Focken et al., "Synthesis of iridium complexes with new planar chiral chelating phosphinyl-imidazolylidene ligands and their application in asymmetric hydrogenation," *Tetrahedron: Asymmetry*, 2004, 15, pp. 1693-1706.

Reich et al., "Macro Rings. XXVII. Multiple Electrophillic Substitution Reactions of [2.2]Paracyclophanes and Interconversions of Polysubstituted Derivatives," *Journal of the American Chemical Society*, Jun. 18, 1969, 91:13, pp. 3527-2533.

Bolm et al., "Synthesis of iridium complexes with novel planar chiral chelating imidazolylidene ligands," *Tetrahedron: Asymmetry*, 2003, 14, pp. 1733-1746.

Bolm et al., The Synthesis of *Pseudo-Germinal, Pseudo-Ortho* and *Ortho* Hydroxy-oxazolinyl[2.2]paracyclophanes for Use as Ligands in Asymmetric Catalysis, *Adv. Synth. Catal.*, 2006, 348, pp. 3093-2100.

Amthor et al., "[2.2]Paracyclophane-Bridged Mixed-Valence Compounds: Application of a GMH Three-Level Model," *J. Phys. Chem. A, Supporting Information*, 2006, 110 (3), pp. S1-S7.

* cited by examiner

PARACYCLOPHANE-BASED LIGANDS, THEIR PREPARATION AND USE IN CATALYSIS

CROSS-REFERENCE TO RELATED APPLICATIONS

This application is the U.S. National Phase filing of PCT International Application No. PCT/GB2008/050730, filed Aug. 21, 2008, and claims priority of British Patent Application No. 0716714.1, filed Aug. 29, 2007, the disclosures of both of which are incorporated herein by reference in their entirety.

FIELD OF THE INVENTION

This invention relates to ligands used in transition metal-catalysed reactions and in particular to substituted paracyclophanes.

BACKGROUND OF THE INVENTION

Paracyclophanes and in particular [2.2]-paracyclophane derivatives are established ligands for transition metal-catalysed asymmetric reactions (see for example, S. E. Gibson and J. D. Knight, Org. Biomol. Chem., 2003, 1, 1256-1269). Of these, paracyclophane bis(phosphines) have attracted considerable attention because catalysts derived from them show high levels of activity and selectivity in a number of useful asymmetric transformations.

For example, WO 97/47632 describes paracyclophane bis(phosphine) ligands and rhodium (Rh), ruthenium (Ru), iridium (Ir) or palladium (Pd) catalysts derived therefrom for asymmetric hydrogenation, isomerization, hydroboration, cyclization, arylation, alkylation and amination reactions. The ligands described have the formula depicted below;

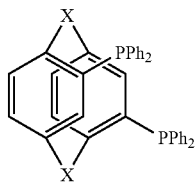

X = —(CH$_2$)$_n$—  ;   —CH$_2$OCH$_2$—  ;   —CH$_2$SO$_2$CH$_2$—

Where both X groups are the identical, these ligands posses $C_2$ symmetry, that is they are chiral and have a $C_2$ axis of symmetry. For example, the $C_2$-symmetric [2.2]ligand where X=—(CH$_2$CH$_2$)—, known as PHANEPHOS, may be used in the asymmetric hydrogenation of ketones when comprising part of a Ru-diamine complex (see WO 01/74829).

WO 02/057278 describes paracyclophane ligands structurally related to the paracyclophane bis(phosphines) where the phenyl groups bound to the phosphorus in the [2.2]paracyclophane structure are replaced by oxygen, nitrogen, chloride or hydrogen atoms. These ligands are depicted below;

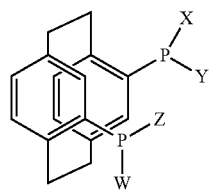

X, Y, Z, W = O; paracyclophane phosphonites
X, Y, Z, W = N; paracyclophane phosphorus-amides
X, Z = O, Y, W = N; paracyclophane phosphonamidite
X, Y, Z, W = Cl; bis(dischlorophosphino) paracyclophane
X, Y, Z, W = H; diphosphino paracyclophane Rh, Ir and Ru catalysts derived therefrom were used in asymmetric hydrogenation reactions.

WO 2004/111065 describes substituted paracyclophanes of formula (I)

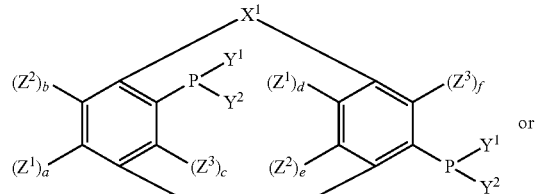

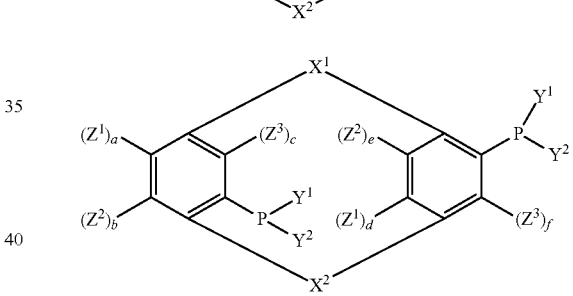

wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, $Z^1$, $Z^2$ and $Z^3$ are substituting groups that optionally contain functional groups, a, b, c, d, e and f are 0 or 1 and a+b+c+d+e+f=1 to 6. Preferably $X^1$ and $X^2$ are —(C$_2$H$_4$)— and a+b+c+d+e+f=1 or 2.

Whereas the paracyclophane ligands described are effective for many asymmetric transformations there is still a need to improve the activity and selectivity of catalysts derived from them over a broader range of reactions and substrates.

The above ligands rely on the dual functionality provided by the two phosphorus atoms to provide the desired selectivity. We have found surprisingly that certain paracyclophanes comprising only one phosphorus moiety are useful ligands.

SUMMARY OF THE INVENTION

Accordingly the present invention provides a substituted paracyclophane of formula (I)

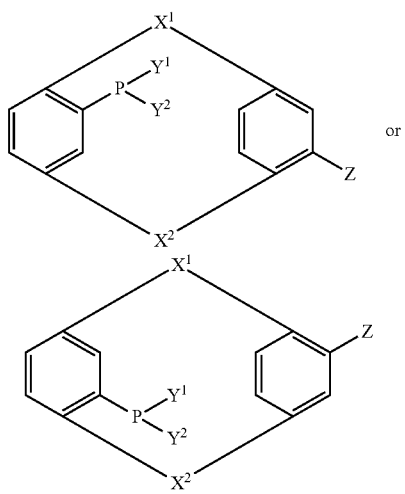

(I)

wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl and Z is a substituted or unsubstituted alkyl group, aryl group or heteroaryl group.

Linking groups $X^1$ and $X^2$ provide links between the benzene rings of the paracyclophane structure that comprise between 2 and 4 carbon atoms. Hence $X^1$ and $X^2$ may be linear, branched or cyclic structures where the link is formed via 2, 3 or 4 carbon atoms. The links may, in addition to the carbon atoms, contain heteroatoms such as O, N or S (where the N atom may in turn be bonded to an alkyl group such as $CH_3$, $C_2H_5$, $C_3H_7$ or $C_4H_9$ or an aryl group, and the S atom may be bonded to an alkyl or aryl group or be part of an SO or $SO_2$ moiety) and/or the carbon atoms in the linking group may be substituted with a halide, e.g. one or more fluorine atoms. Hence linking groups $X^1$ and $X^2$ may independently be for example $-(CH_2)_{2-4}-$, $-CH_2OCH_2-$, $-CH_2N(CH_3)CH_2-$, $-CH_2SO_2CH_2-$, $-C_2F_4-$ or ortho, meta or para $-C_6H_4$ Such modification of the linking group may be useful for adapting the substituted paracyclophane to different reaction conditions, e.g. solvents. Preferably the linking groups comprise $-(C_2H_4)-$, $-(C_3H_6)-$ or $-(C_4H_8)-$. More preferably $X^1$ and $X^2$ are the same and most preferably $X^1$ and $X^2$ are both $-(C_2H_4)-$.

DETAILED DESCRIPTION OF THE INVENTION

In one embodiment the paracyclophane is a bis(phosphine) where $Y^1$ and $Y^2$ may independently be hydrogen, halide (Cl, Br, F or I) or straight chain or branched alkyl groups (e.g. C1-C20) such as methyl, ethyl, propyl, iso-propyl, butyl, iso-butyl, sec-butyl, tert-butyl, pentyl, hexyl, heptyl, octyl, nonyl, decyl, dodecyl, and stearyl, cycloalkyl groups (e.g. C3-C10) such as cyclopropyl, cyclobutyl, cyclopentyl, cyclohexyl or adamantyl, or aryl groups such as phenyl, naphthyl or anthracyl. The alkyl groups may be optionally substituted with one or more substituents such as halide (Cl, Br, F or I) or alkoxy groups, e.g. methoxy, ethoxy or propoxy groups. The aryl groups may be optionally substituted with one or more substituents such as halide (Cl, Br, F or I), methyl, trifluoromethyl or methoxy groups. Suitable substituted aryl groups include 4-methylphenyl, 3,5-dimethylphenyl, 4-methoxyphenyl and 4-methoxy-3,5-dimethylphenyl. Substituted or unsubstituted heteroaryl groups such as pyridyl may also be used. In an alternative embodiment, $Y^1$ and $Y^2$ on each phosphorus atom may be linked so as to form a ring structure incorporating the phosphorus atom. In such an embodiment, preferably $Y^1$ and $Y^2$ are linked so as to provide each phosphorus atom in a 4- to 7-membered ring. In yet a further embodiment, the paracyclophane may be a phosphonite (where $Y^1$ and $Y^2$ are oxygen atoms), a phosphorus-amide (where $Y^1$ and $Y^2$ are nitrogen atoms), or a phosphonamidite (where $Y^1$ is an oxygen atom and $Y^2$ is a nitrogen atom). Preferably, $Y^1$ and $Y^2$ are the same and are cyclohexyl, phenyl or substituted phenyl groups.

In formula (I), Z is a substituted or unsubstituted alkyl group, aryl group or heteroaryl group. The substituted or unsubstituted alkyl group may be a substituted or unsubstituted C1-C30, preferably a substituted or unsubstituted C1-C10 alkyl group, which may be cyclic, branched or linear, such as methyl, ethyl, n-propyl, isopropyl, n-butyl, iso-butyl, sec-butyl, tert-butyl, n-pentyl, hexyl, cyclohexyl, n-octyl, iso-octyl, 2-ethylhexyl, n-nonyl, iso-decyl, undecyl or octadecyl. The substituted or unsubstituted aryl group Z may be a substituted or unsubstituted phenyl, naphthyl or anthracyl group. The substituted or unsubstituted heteroaryl group may be a substituted or unsubstituted furan, thiophen, morpholine, pyrrole, pyridine or quinoline group.

Substituting groups may be one or more of halide (e.g. F, Cl, Br, I), hydroxyl, C1-30 alkoxy, carbonyl, carboxyl, anhydride, methacryl, epoxide, vinyl, nitrile, nitro, sulphate, sulphonyl, mercapto, amino, amine, imine, amide and imide.

In a preferred embodiment, Z is a substituted aryl group having one or more substituting groups selected from halide (e.g. F, Cl, Br, I), hydroxyl, C1-30 alkoxy, carbonyl, carboxyl, anhydride, methacryl, epoxide, vinyl, nitrile, nitro, sulphate, sulphonyl, mercapto, amino, amine, imine, amide and imide. Preferred substituting groups are halide (e.g. F, Cl, Br, I), hydroxyl, C1-C10 alkoxy, carbonyl (CHO), carboxyl ($CO_2H$), nitrile (CN), amino ($NH_2$) and amine (NHR or $NR_2$) where R is C1-10 alkyl or aryl. Alkoxy groups, e.g. methoxy groups, are particularly preferred. The substituted aryl group Z may be mono-, di-, tri-, tetra- or penta-substituted. The substituting groups on Z may be the same or different. In a particularly preferred embodiment Z is a 2,5-disubstituted phenyl group, especially a 2,5-dimethoxy phenyl group.

The substituted paracyclophane of the present invention may be prepared by substitution reactions on a suitable paracyclophane intermediate. In particular, we have found that substituted pseudo-ortho dibromo-paracyclophane provides a very useful starting point for the synthesis of the substituted paracyclophane of the present invention.

Accordingly, the present invention further provides a method for preparation of a substituted paracyclophane of formula (I), by

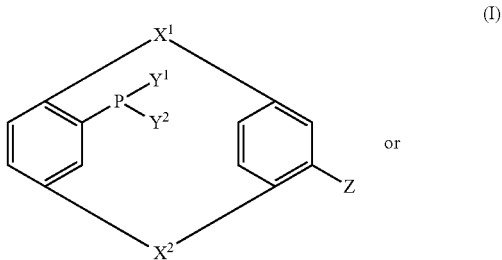

(I)

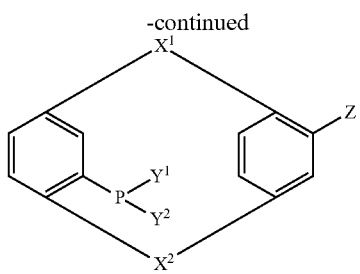

(a) performing a substitution reaction on a pseudo-ortho dibromoparacyclophane to form an intermediate substituted bromoparacyclophane of formula (II), and

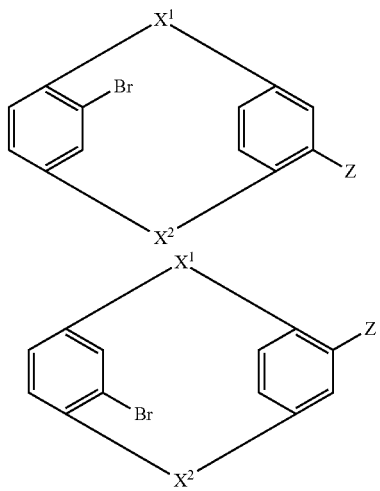

(b) reacting the substituted bromoparacyclophane of formula (II) with a phosphorus compound comprising $P(Y^1Y^2)$, wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl or heteroaryl, and Z is a substituted or unsubstituted alkyl group, aryl group or heteroaryl group.

Accordingly, the invention further provides a substituted bromoparacyclophane of formula (II)

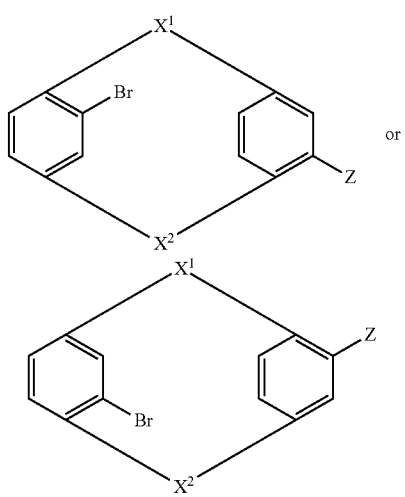

wherein $X^1$ and $X^2$ are linking groups comprising between 2 to 4 carbon atoms, and Z is a substituted or unsubstituted alkyl group, aryl group or heteroaryl group.

The pseudo-ortho dibromoparacyclophane from which the substituted bromoparacyclophane (II) is synthesised may be prepared according to known methods. Typically a paracyclophane may be reacted with bromine in the presence of iron in a suitable solvent (see D. J. Cram et al, *J. Am. Chem. Soc.*, 1969, 91, (13), 3527). In particular, for commercially available [2.2]paracyclophane, the synthesis of the pseudo-ortho dibromo[2.2]paracyclophane may be performed according to the methods described in example 1 and example 2 on pages 31 and 32 of aforesaid WO 97/47632.

Preferably the substitution reaction is performed using a boronic acid, of formula Z—B(OH)$_2$, in which Z may be substituted or unsubstituted. This reaction, which is analogous to a Suzuki C—C coupling reaction, may be performed using a palladium catalyst in the presence of potassium phosphate in a suitable solvent at reflux under nitrogen. This reaction is depicted below;

Scheme 1

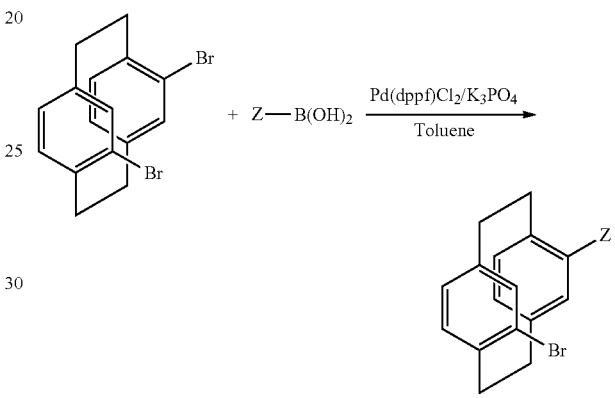

Surprisingly the mono-substituted product forms in high yield.

Once the substituted bromoparacyclophane (II) has been synthesised, the next step of the method of the present invention is the conversion of the remaining pseudo-ortho bromide group to the desired phosphine, phosphonite, phosphorus amide or phosphonamidite by reacting the substituted bromoparacyclophane (II) with a phosphorus compound comprising $P(Y^1Y^2)$. This reaction may be performed according to a number of known methods.

Preferably, substituted paracyclophane mono(phosphines) are prepared by treating the substituted bromoparacyclophane of formula (II) with an alkyl lithium reagent, e.g. tert-Butyl Lithium (tBuLi) in a suitable solvent at low temperature and the anion quenched with an aryl-, alkyl, or cycloalkyl-phosphinylchloride, e.g. dicyclohexylphosphinylchloride (Cy$_2$PCl) to give the desired substituted paracyclophane mono(phosphine). A similar method may be used for other aryl and alkyl phosphines. An example of this reaction is depicted as follows;

Scheme 2

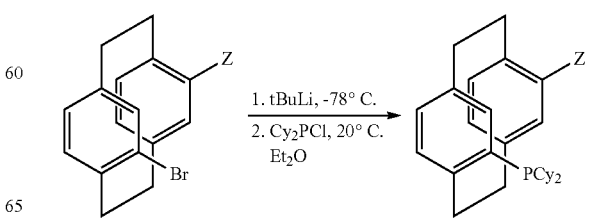

Alternatively, the more air and moisture-stable corresponding phosphine oxide may be prepared using Ph$_2$POCl and the phosphine oxide subsequently reduced using e.g. HSiCl$_3$.

Methods suitable for preparing a phosphonite, phosphorus amide and phosphonamidite from the substituted bromoparacyclophane of formula (II) may be found in A. Zanotti-Gerosa et al, *Org. Lett.*, 2001, 3687. For example. a substituted bromoparacyclophane may be converted to the corresponding substituted paracyclophane mono(phosphonite) in an analogous manner to the phosphine by direct metallation of the substituted bromoparacyclophane (II) with a strong organometallic base and reaction with the appropriate chloro-phosphonite. The substituted paracyclophane mono(phosphonite) may be synthesised by treatment of a substituted paracyclophane mono(dichlorophosphine) or substituted paracyclophane phosphorus-diamide with an alcohol, diol or metal diolate. The substituted paracyclophane mono(dichlorophosphine) may itself be obtained via the paracyclophane phosphorus diamide which may be prepared by direct metallation of the substituted bromoparacyclophane (II) with a strong organometallic base and reaction with a chloro-phosphorus-diamide such as Cl—P(NCH$_3$)$_2$ or ClP(iso-C$_3$H$_7$). The resulting paracyclophane phosphorus-diamide may be converted to the paracyclophane mono(dichlorophosphine) by treatment with an HCl solution.

The substituted paracyclophane of the present invention is chiral and may adopt one of two enantiomeric forms i.e. an (R)- or (S)-configuration. Accordingly, the paracyclophane may comprise a racemic mixture of enantiomers. Alternatively and preferably the substituted paracyclophane comprises a substantially enantiomerically-pure enantiomer (i.e having an enantiomeric excess >75%, preferably >95%). To obtain a substantially pure enantiomer the substituted paracyclophane may be prepared from a substantially enantiomerically-pure pseudo-ortho dibromoparacyclophane starting material. For example, resolution of a racemic mixture of pseudo-ortho dibromoparacyclophane may be effected on a chiral stationary phase such as crystalline cellulose triacetate using ethanol as eluant or on chiral HPLC columns. Alternatively, a chiral resolution may be performed at later stages during the synthetic process. For example, the resolution may be performed on the substituted paracyclophane mono(phosphine), phosphine oxide, phosphonite, phosphorus amide or phosphonamidite (I) using known crystallisation techniques or separation on chiral chromatography columns.

It will be understood by those skilled in the art that where one enantiomer of a substituted paracyclophane is depicted, the other is included within the scope of the present invention.

The substituted paracyclophane (I) of the present invention may be used as a ligand to prepare metal complexes suitable for use as catalysts in chemical reactions.

Accordingly, the invention further provides a metal complex comprising the reaction product of a metal compound and a substituted paracyclophane of formula (I)

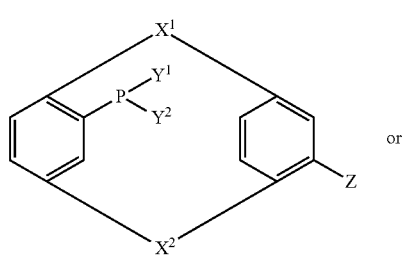

(I)

or

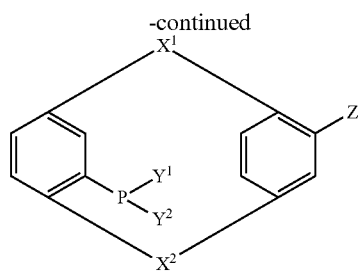

-continued wherein X$^1$ and X$^2$ are linking groups comprising between 2 to 4 carbon atoms, Y$^1$ and Y$^2$ are selected from the group consisting of hydrogen, halide, oxygen, nitrogen, alkyl, cycloalkyl, aryl or heteroaryl, and Z is a substituted or unsubstituted alkyl group, aryl group or heteroaryl group.

The substituted paracyclophane (I) may be combined with the metal compound in a racemic mixture or in a substantially enantiomerically pure form. Preferably the substituted paracyclophane (I) is substantially enantiomerically-pure (i.e having an enantiomeric excess >75%, preferably >95%). The metal compound may be any metal compound that is able to react with the substituted paracyclophane (I) to provide a metal complex. The metal compound is preferably a compound of palladium (Pd), platinum (Pt), rhodium (Rh), iridium (Ir) or ruthenium (Ru), which may be a metal salt, e.g. halide, carboxylate, sulphonate or phosphonate, or an organometallic compound. The metal complex may additionally comprise ligands that are able to reversibly co-ordinate. Reversibly co-ordinating ligands may improve the stability of the metal complexes and may be provided during the synthesis of the metal complex or may react with the metal complex when it is added to the reaction mixture. By "reversibly co-ordinating" we mean a ligand that can be readily displaced by other molecules in a reaction mixture. Such reversibly co-ordinating ligands may be selected from the list comprising dienes, particularly cyclic dienes such as cyclooctadiene or norbornadiene, C1-C4 alcohols, ethers, cyclic ethers, diols, e.g. 1,2-diols and C2 or C3 olefins, e.g. ethylene. In addition, the metal complex may additionally comprise a non-reversibly co-ordinating ligand that may be used to modify the reactivity and selectivity of the metal complex catalyst. Non-reversibly co-ordinating ligands that may be used are diamines, for example 1,2-diphenylethylenediamine, 1,2-cyclohexylethylenediamine and ethylene diamine and particularly substantially enantiomerically-pure chiral 1,2-diamines such as (S,S)-1,2-diphenylethylenediamine.

To satisfy the oxidation state of the metal complex, it may when the oxidation state of the metal requires, further comprise a counter-ion. The counter-ion may be any suitable anion but is preferably a non-nucleophile anion selected from trifluoromethanesulphonate (triflate or OTf), perchlorate (ClO$_4$), hexafluoroantimonate (SbF$_6$) or hexafluorophosphate (PF$_6$).

The metal complexes may be readily prepared from the substituted paracyclophane of the present invention. In general, the metal compound is combined with the substituted paracyclophane and optionally the reversibly co-ordinating ligand and/or non-reversibly co-ordinating ligand in a suitable solvent and heated if necessary to form the desired metal complex.

The substituted paracyclophane ligands of the present invention may be racemic or chiral, and when chiral, are able to produce chiral metal complex catalysts. The chiral metal complex catalysts of the present invention may be applied to a large number of reactions used to produce chiral or non-chiral products. Such reactions include but are not limited to asymmetric hydrogenation reactions such as the chiral hydrogenation of enamide and non-enamide structures, asymmetric hydrogenation in iso-quinoline synthesis, the asymmetric hydrogenation of unsaturated alcohols, and the asymmetric hydrogenation of ketones and imines.

The catalysts of the present invention may also be used for carbon-carbon coupling reactions such as the Heck or Suzuki reactions, for the enantioselective isomerization of olefins, asymmetric hydroboration reactions, asymmetric cyclisation of olefinic aldehydes, asymmetric arylation and alkylation reactions and the amination of aryl halides (Hartwig-Buchwald reaction).

Where appropriate, to achieve high levels of enantiomeric purity in a reaction it is preferred that the metal complex comprises a substantially enantiomerically-pure substituted paracyclophane (I).

The conditions for using the metal complex catalysts are typically similar to those used for structurally related catalysts. The metal complex may be formed as a catalyst in situ, or separately synthesised.

While we have found the metal complexes comprising substituted paracyclophanes of the present invention to be effective homogeneous catalysts it may be desirable to provide such metal complexes on solid supports as heterogeneous catalysts. Heterogeneous catalysts have the advantages that they are often easier to separate from the reaction mixtures and may in some circumstances be recycled. To form a heterogeneous catalyst, the metal complex may be absorbed or ion-exchanged into a suitable solid support material, e.g. a zeolite. Alternatively the metal complex may be reacted with functional groups present on a solid support material to form a covalently bound catalyst. The solid support materials to which the substituted paracyclophane may be attached, may be polymers, metal oxides or sol-gel materials that have sites capable of reacting with the metal complex.

The invention is further illustrated by reference to the following examples where
dppf=1,1'-bis(diphenylphosphino)ferrocene,
dba=dibenzylideneacetone,
Cy=cyclohexyl, and
room temperature=20-25° C. unless otherwise stated.

The nomenclature of the substituted paracyclophanes was assigned as in: S. Gisbon et al. *Organic and Biomolecular Chemistry* 2003, 1256.

Example 1

Synthesis of a Monophosphine Ligand (a) Preparation of a Substituted Bromoparacyclophane

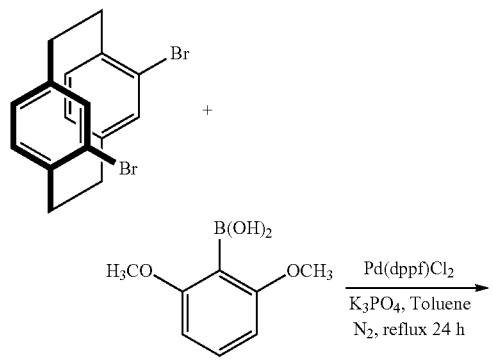

-continued

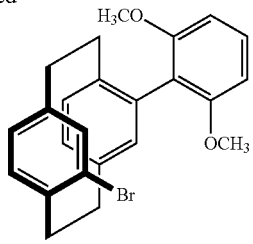

To a Schlenk tube were added (rac)-4,12-dibromoparacyclophane 1.83 g (5.0 mmol), 2,6-dimethoxyphenylboronic acid 1.37 g (7.5 mmol, 1.5 equiv), Pd(dppf)Cl$_2$ 164 mg (0.20 mmol, 4 mol %), and K$_3$PO$_4$ 2.12 g (10.0 mmol, 2.0 equiv). The flask was evacuated and backfilled with nitrogen three times. Fresh distilled toluene (20 mL) was introduced, and the flask was sealed, stirred at reflux for 24 h. The reaction mixture was cooled, diluted with toluene (30 mL), and hydrolyzed with 10% NaOH (30 mL). Separated and extracted the water phase with EtOAc (3×25 mL). The organic layers were dried over MgSO$_4$ and concentrated under reduced pressure. The residue was purified by column chromatography (EtOAc/hexane, 30:1) on silica gel to afford white solid products 1.82 g (86% yields). $^1$H NMR (400 MHz, CDCl$_3$) δ7.24 (t, J=8.4 Hz, 1H), 7.10 (s, 1H), 7.75 (d, J=8.4 Hz, 1H), 6.73 (s, 1H), 6.67 (s, 2H), 6.54-6.51 (m, 2H), 6.39 (d, J=7.6 Hz, 1H), 4.10 (s, 3H), 3.60-3.51 (m, 1H), 3.48 (s, 3H), 3.22-3.10 (m, 2H), 2.95-2.75 (m, 4H), 2.65-2.55 (m, 1H); $^{13}$C NMR (100 MHz, CDCl$_3$) δ 158.6, 158.5, 141.5, 140.8, 139.7, 137.4, 137.1, 134.6, 133.5, 133.0, 131.6, 131.2, 129.8, 129.0, 126.9, 118.5, 105.1, 105.0, 56.5, 55.8, 37.3, 34.9, 34.8, 32.9; MS m/z 442: 440=1:1 (M+NH$_3$, 100), 425: 423=1:1 (M+H, 72).

(b) Conversion to the Monophosphine

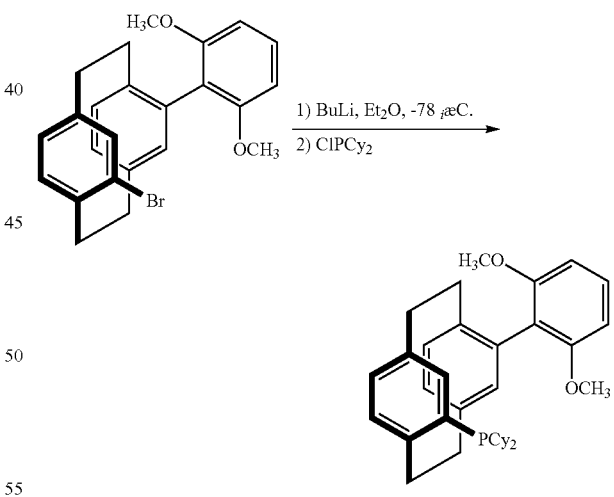

An oven-dried Schlenk flask was charged with 4-bromo-12-(2',6'-dimethoxy)phenyl-paracyclophane 1.06 g (2.5 mmol), evacuated and backfilled with nitrogen three times, then 50 mL fresh distilled Et$_2$O was introduced. After cooled to −78° C., 1.3 mL (3.25 mmol, 2.5 M in hexane) n-BuLi was dropwise added. Stirred at −78° C. for 2 h, and gradually warmed to room temperature for another 3 h. 0.66 mL (3 mmol) ClPCy$_2$ was added, the reaction mixture was stirred at room temperature overnight. Added 0.5 mL 1 M NaOH and stirred for 10 min, removed the solvent. The crude product was purified by flash column chromatography (hexane) on silica gel, and 0.89 g (66% yields) white solid products obtained. $^1$H NMR (400 MHz, CDCl$_3$) δ 7.19 (t, J=8.4 Hz, 1H), 6.77-6.66 (m, 4H), 6.51-6.46 (m, 3H), 6.43 (s, 1H), 4.05 (s, 3H), 4.05-4.01 (m, 1H), 3.37 (s, 3H), 3.25-2.88 (m, 6H), 2.85-2.77 (m, 1H), 2.08-2.03 (m, 1H), 1.98-1.93 (m, 1H), 1.80-1.63 (m, 6H), 1.48-1.43 (m, 3H), 1.30-0.73 (m, 11H); $^{13}$C NMR (100 MHz, CDCl$_3$) δ 159.4, 157.7, 146.7, 146.5, 138.2, 137.4, 135.0, 134.8, 134.6, 134.5, 133.8, 133.4, 133.3, 130.7, 128.4, 118.5, 105.1, 104.0, 56.5, 55.2, 37.3, 37.1, 34.9, 34.8, 34.2, 32.0, 30.9, 29.1, 28.7, 28.2, 27.6, 27.5, 27.2, 26.7; $^{31}$P NMR (162 MHz, CDCl$_3$) δ-1.72; MS m/z 541 (M+H, 100); Anal. Calcd for C$_{36}$H$_{45}$O$_2$P: C, 79.97; H, 8.39. Found: C, 79.97; H, 8.44.

Example 2

Catalysis (a) Amination of Aryl Chlorides (Buchwald-Hartwig C—N Coupling Reaction).

An oven-dried carousel reaction tube was loaded with 4.6 mg Pd$_2$(dba)$_3$ (0.005 mmol, 0.5 mol %), 10.8 mg ligand of Example 1 (0.02 mmol, 2 mol %), and 135 mg NaOtBu (1.4 mmol, 1.4 equiv), then evacuated and backfilled with nitrogen three times. Fresh distilled dioxane (4 mL), aryl chloride (1 mmol), and amine (1.2 mmol) were added successively. The tube was sealed, and the reaction mixture was stirred at 100° C. for the mentioned time. After the mixture was cooled to room temperature, 15 mL of EtOAc was added and the mixture was washed with 5 mL of brine. The organic layer was dried over MgSO$_4$ and concentrated under reduced pressure. The crude product was purified by flash column chromatography on basic Al$_2$O$_3$.

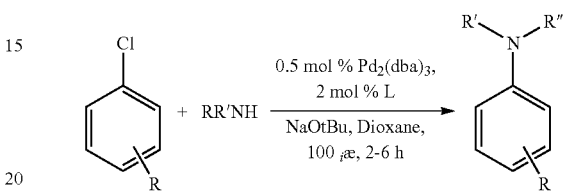

| Entry | ArCl | Amine | Product | Time/h | Yield/% |
|---|---|---|---|---|---|
| 1 | 4-methylphenyl chloride | | 4-methylphenyl morpholine | 2 | 95 |
| 2 | 4-MeO-phenyl chloride | | 4-MeO-phenyl morpholine | 3 | 94 |
| 3 | 4-NC-phenyl chloride | | 4-NC-phenyl morpholine | 3 | 88 |
| 4 | 3-MeO-phenyl chloride | | 3-MeO-phenyl morpholine | 2 | 97 |
| 5 | 2-methylphenyl chloride | morpholine | 2-methylphenyl morpholine | 3 | 85 |
| 6 | 2-CN-phenyl chloride | | 2-CN-phenyl morpholine | 3 | 65 |
| 7 | 2,6-dimethylphenyl chloride | | 2,6-dimethylphenyl morpholine | 6 | 60 |
| 8 | phenyl chloride | aniline | diphenylamine | 5 | 91 |

-continued

| Entry | ArCl | Amine | Product | Time/h | Yield/% |
|---|---|---|---|---|---|
| 9 | 4-chlorotoluene | benzylamine | N-benzyl-4-methylaniline | 3 | 93 |
| 10 | 4-chlorotoluene | 1-phenylethylamine | N-(1-phenylethyl)-4-methylaniline | 3 | 90 |
| 11 | 4-chlorotoluene | aniline | 4-methyl-N-phenylaniline | 5 | 89 |
| 12 | 4-chlorotoluene | N-ethylaniline | N-ethyl-N-phenyl-4-methylaniline | 5 | 81 |
| 13 | 4-chlorotoluene | n-butylamine | N-butyl-4-methylaniline | 5 | 93 |

(b) Suzuki Coupling of Aryl Chlorides.

An oven-dried carousel reaction tube was charged with boronic acid (1.5 mmol), K$_3$PO$_4$ (637 mg, 3 mmol), and ligand of Example 1 (1.1 mg, 0.002 mmol, 0.2 mol %). The reaction vessel was evacuated and backfilled with nitrogen. This process was repeated five times. Through a rubber septum, aryl chloride (1 mmol), 0.5 mL Pd(OAc)$_2$ solution (2×10$^{-3}$ M in dioxane, 0.001 mmol, 0.1 mol %), and fresh distilled dioxane (4.5 mL) were introduced. The tube was sealed, and the reaction mixture was stirred at 80° C. for 12 h. After the mixture was cooled to room temperature, 15 mL of EtOAc was added and the mixture was washed with 5 mL of brine. The organic layer was dried over MgSO$_4$ and concentrated under reduced pressure. The crude product was purified by flash column chromatography on silica gel.

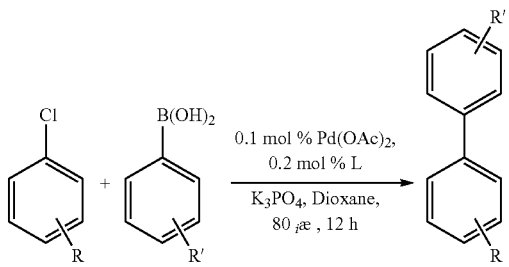

| Entry | ArCl | ArB(OH)$_2$ | Product | Yield/% |
|---|---|---|---|---|
| 1 | 2-chlorotoluene | phenylboronic acid | 2-methylbiphenyl | 90 |
| 2 | 2-chloroanisole | phenylboronic acid | 2-methoxybiphenyl | 87 |

-continued

| Entry | ArCl | ArB(OH)₂ | Product | Yield/% |
|---|---|---|---|---|
| 3 | 2-chlorobenzonitrile | | 2-cyanobiphenyl | 90 |
| 4 | 2-chloro-5-methoxybenzene | PhB(OH)₂ | 3-methoxybiphenyl | 96 |
| 5 | 4-chlorotoluene | | 4-methylbiphenyl | 92 |
| 6 | 4-chloroanisole | | 4-methoxybiphenyl | 90 |
| 7 | 4-chlorobenzonitrile | | 4-cyanobiphenyl | 96 |
| 8 | 4'-chloroacetophenone | | 4-acetylbiphenyl | 97 |
| 9 | 4-chloroanisole | 4-methoxyphenylboronic acid | 4,4'-dimethoxybiphenyl | 93 |
| 10[a] | 2,6-dimethylchlorobenzene | PhB(OH)₂ | 2,6-dimethylbiphenyl | 86 |
| 11[a] | 2-chlorotoluene | 2-methylphenylboronic acid | 2,2'-dimethylbiphenyl | 84 |
| 12[b] | 1-bromo-2-methoxynaphthalene | 1-naphthylboronic acid | 2-methoxy-1,1'-binaphthyl | 94 |

[a] 0.2 mol % Pd(OAc)₂ and 0.4 mol % L used;
[b] 0.6 mol % Pd(OAc)₂ and 1.2 mol % L used.

The invention claimed is:

1. A substituted paracyclophane of formula (I)

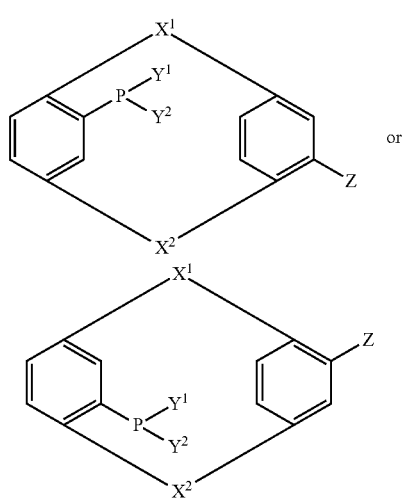

(I)

or wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl and heteroaryl, and Z is an unsubstituted alkyl group, a substituted aryl group, an unsubstituted aryl group, a substituted heteroaryl group, or an unsubstituted heteroaryl group;

wherein when Z is a substituted aryl group, the substituents are selected from the group consisting of halide, hydroxyl alkoxy, carbonyl, carboxyl, anhydride, methacryl, epoxide, vinyl, nitrile, nitro, sulphate, sulphonyl, mercapto, amino, amine, imine, amide and imide.

2. The substituted paracyclophane according to claim 1 wherein $X^1$ and $X^2$ are both —$C_2H_4$—.

3. The substituted paracyclophane according to claim 1 wherein Z is a substituted or unsubstituted phenyl, naphthyl or anthracyl group.

4. The substituted paracyclophane according to claim 1 wherein Z is a substituted aryl group having one or more substituting groups selected from the group consisting of halide, hydroxyl, alkoxy, carbonyl, carboxyl, anhydride, methacryl, epoxide, vinyl, nitrile, nitro, sulphate, sulphonyl, mercapto, amino, amine, imine, amide and imide.

5. The substituted paracyclophane according to claim 1 wherein Z is a 2,5-disubstituted phenyl group.

6. The substituted paracyclophane according to claim 2 wherein Z is a substituted phenyl, naphthyl or anthracyl group.

7. The substituted paracyclophane according to claim 2 wherein Z is a substituted aryl group having one or more substituting groups selected from halide, hydroxyl, alkoxy, carbonyl, carboxyl, anhydride, methacryl, epoxide, vinyl, nitrile, nitro, sulphate, sulphonyl, mercapto, amino, amine, imine, amide and imide.

8. A method for preparation of a substituted paracyclophane of formula (I), comprising the steps of

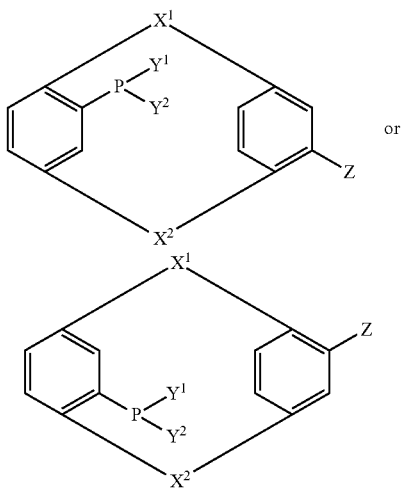

(I)

or (a) performing a substitution reaction on a pseudo-ortho dibromoparacyclophane to form an intermediate substituted bromoparacyclophane of formula (II), and

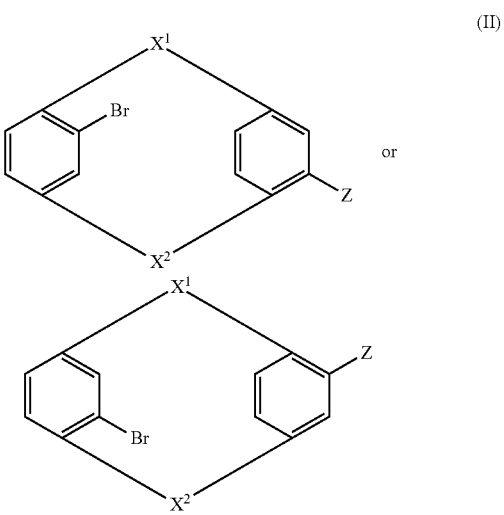

(II)

or (b) reacting the substituted bromoparacyclophane with a phosphorus compound comprising $P(Y^1Y^2)$, wherein $X^1$ and $X^2$ are linking groups comprising between 2 to 4 carbon atoms, $Y^1$ and $Y^2$ are selected from the group consisting of hydrogen, halide, oxygen, nitrogen, alkyl, cycloalkyl, aryl and heteroaryl, and Z is an unsubstituted alkyl group, a substituted aryl group, an unsubstituted aryl group, a substituted heteroaryl group, or an unsubstituted heteroaryl group;

wherein when Z is a substituted aryl group, the substituents are selected from the group consisting of halide, hydroxyl, alkoxy, carbonyl, carboxyl, anhydride, methacryl, epoxide, vinyl, nitrile, nitro, sulphate, sulphonyl, mercapto, amino, amine, imine, amide and imide.

9. The method according to claim 8 wherein the substitution reaction is performed using a boronic acid, of formula Z—$B(OH)_2$, in which Z may be substituted or unsubstituted.

10. The method according to claim 9 wherein the boronic acid comprises a 2,5-disubstituted phenyl group.

11. A substituted bromoparacyclophane of formula (II)

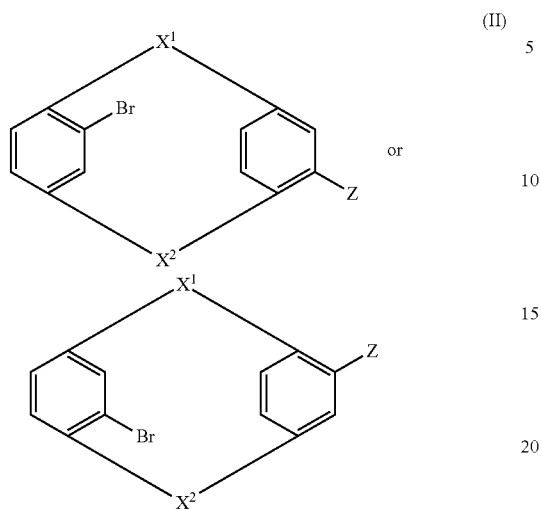

(II)

wherein $X^1$ and $X^2$ are linking groups comprising between 2 to 4 carbon atoms, and Z is a substituted or unsubstituted alkyl group, aryl group or heteroaryl group;

wherein when Z is a substituted aryl group, Z is a 2,5-disubstituted phenyl group.

12. The substituted bromoparacyclophane according to claim 11 wherein Z is a 2,5-disubstituted phenyl group.

* * * * *